United States Patent
Qu et al.

(10) Patent No.: US 9,606,030 B2
(45) Date of Patent: Mar. 28, 2017

(54) METHOD FOR DETECTING CRYSTAL DEFECTS

(75) Inventors: Wei Feng Qu, Annaka (JP); Fumio Tahara, Annaka (JP); Yuuki Ooi, Annaka (JP)

(73) Assignee: SHIN-ETSU HANDOTAI CO., LTD., Tokyo (JP)

(*) Notice: Subject to any disclaimer, the term of this patent is extended or adjusted under 35 U.S.C. 154(b) by 603 days.

(21) Appl. No.: 14/124,827

(22) PCT Filed: Jun. 18, 2012

(86) PCT No.: PCT/JP2012/003953
§ 371 (c)(1),
(2), (4) Date: Dec. 9, 2013

(87) PCT Pub. No.: WO2013/008391
PCT Pub. Date: Jan. 17, 2013

(65) Prior Publication Data
US 2014/0119399 A1    May 1, 2014

(30) Foreign Application Priority Data
Jul. 14, 2011 (JP) .................................. 2011-155910

(51) Int. Cl.
*G01N 25/72* (2006.01)
*G01N 1/28* (2006.01)
*H01L 21/66* (2006.01)

(52) U.S. Cl.
CPC ............... *G01N 1/28* (2013.01); *H01L 22/12* (2013.01); *H01L 22/24* (2013.01)

(58) Field of Classification Search
USPC ............................................................ 374/5
See application file for complete search history.

(56) References Cited

U.S. PATENT DOCUMENTS 5,841,532 A * 11/1998 Yoshida ............. G01N 21/6489
356/300
6,544,490 B1   4/2003 Takeno et al.
(Continued)

FOREIGN PATENT DOCUMENTS

| JP | A-2001-139396 | 5/2001 |
| JP | A-2002-246429 | 8/2002 |

(Continued)

OTHER PUBLICATIONS

International Search Report issued in International Patent Application No. PCT/JP2012/003953 dated Aug. 21, 2012.

*Primary Examiner* — Lisa Caputo
*Assistant Examiner* — Nasir U Ahmed
(74) *Attorney, Agent, or Firm* — Oliff PLC (57) ABSTRACT

A method for detecting a crystal defect in a silicon single crystal wafer doped with nitrogen, the silicon single crystal wafer whose initial oxygen concentration is 8 ppma (JEIDA) or lower. The method further includes the steps of: making a crystal defect of defect size of 25 nm or smaller apparent and detectable by implanting oxygen into the crystal defect by performing heat treatment on the silicon single crystal wafer in an oxygen atmosphere; and detecting the crystal defect of the silicon single crystal wafer after the heat treatment temperature is set such that, when the ratio between the oxygen solid solubility and the initial oxygen concentration of the silicon single crystal wafer heat treatment is set at α=the oxygen solid solubility/the initial oxygen concentration, α falls within a range from 1 to 3.

8 Claims, 5 Drawing Sheets

(56) References Cited

U.S. PATENT DOCUMENTS

| | | | | |
|---|---|---|---|---|
| 6,878,451 | B2* | 4/2005 | Asayama | C30B 15/00 |
| | | | | 117/930 |
| 7,875,115 | B2* | 1/2011 | Nakai | C30B 29/06 |
| | | | | 117/13 |
| 8,092,867 | B2* | 1/2012 | Karshtedt | C08G 77/60 |
| | | | | 427/387 |
| 2003/0059635 | A1* | 3/2003 | Naasani | B82Y 15/00 |
| | | | | 428/473.5 |
| 2003/0116082 | A1* | 6/2003 | Sakurada | C30B 15/14 |
| | | | | 117/20 |
| 2005/0127477 | A1* | 6/2005 | Takase | H01L 21/3225 |
| | | | | 257/550 |
| 2007/0231932 | A1 | 10/2007 | Reynaud et al. | |
| 2008/0035898 | A1* | 2/2008 | Tsuchiya | C09K 11/7787 |
| | | | | 252/600 |
| 2010/0051945 | A1* | 3/2010 | Umeno | C30B 15/203 |
| | | | | 257/49 |
| 2012/0043644 | A1* | 2/2012 | Ono | C30B 29/06 |
| | | | | 257/607 |

FOREIGN PATENT DOCUMENTS

| | | |
|---|---|---|
| JP | A-2007-273977 | 10/2007 |
| JP | A-2010-132509 | 6/2010 |

* cited by examiner

FIG. 5

(a) NO REVEALING HEAT TREATMENT (b) 900°C/30 MINUTES
$\alpha = 0.75$ (c) 1000°C/30 MINUTES
$\alpha = 1$ (d) 1100°C/30 MINUTES
$\alpha = 1.5$ (e) 1220°C/30 MINUTES
$\alpha = 3$ (f) 1250°C/30 MINUTES
$\alpha = 3.5$

METHOD FOR DETECTING CRYSTAL DEFECTS

TECHNICAL FIELD

The present invention relates to a method for detecting a crystal defect of a silicon single crystal wafer and, in particular, to a method for detecting a crystal defect by making the crystal defect apparent.

BACKGROUND ART

In a silicon single crystal, a crystal defect size tends to be reduced when an oxygen concentration is reduced. For example, in a silicon single crystal wafer obtained by slicing a silicon single crystal of low oxygen concentration, such as a silicon single crystal in which an initial interstitial oxygen concentration is 8 ppma or lower, in particular, 5 ppma or lower, it is difficult to detect micro crystal defects such as a BMD (Bulk Micro Defect), a COP (Crystal Originated Particle), and a "void", which makes it extremely difficult to make a judgment about a defect region as to whether a silicon single crystal wafer obtained by slicing is a defect-free region or not.

For a crystal defect that is difficult to detect due to a minute size thereof, a method for detecting such a crystal defect by making the crystal defect apparent has been known.

For example, in Patent Literature 1, a method for evaluating a silicon wafer, the method for evaluating a silicon wafer wherein heat treatment that grows oxygen precipitates without generating new oxygen precipitates is performed on a silicon wafer containing oxygen precipitates that are smaller than the lower limit size of an oxygen precipitate that can be detected by a particular measuring apparatus in order to grow all the oxygen precipitates that are smaller than the lower limit size to a size that can be detected by the particular measuring apparatus and then an oxygen precipitate density in the silicon wafer is measured by the particular measuring apparatus is described.

Moreover, in Patent Literature 2, a method for revealing crystal defects in bulk silicon substrate, the method that performs heat treatment called "revealing heat treatment" that is conducted in a non-reducing atmosphere at a temperature in the range from 500° C. to 1300° C., is described. Specifically, the "revealing heat treatment" is performed in an atmosphere of oxygen, argon, nitrogen, or a mixture of two of them.

CITATION LIST

Patent Literatures

Patent Literature 1: Japanese Unexamined Patent Application Publication No. 2002-246429
Patent Literature 2: Japanese Unexamined Patent Application Publication No. 2007-273977

SUMMARY OF INVENTION

Technical Problem

However, with the above-described methods of Patent Literatures 1 and 2, it has become difficult to detect micro crystal defects such as a BMD, a COP, and a "void" in a silicon single crystal wafer (a low-oxygen wafer) of low oxygen concentration. In particular, in a low-oxygen wafer doped with nitrogen, the low-oxygen wafer whose oxygen concentration is 8 ppm or lower, a defect size is further reduced, which makes it impossible to detect a micro defect such as a "void", in particular, the micro defect smaller than or equal to 25 nm, with the current defect evaluation methods.

The present invention has been made in view of these problems, and an object thereof is to provide a method for detecting a crystal defect, the method that can detect a crystal defect of particularly small size, the crystal defect present in a silicon single crystal wafer doped with nitrogen, the silicon single crystal wafer of low oxygen concentration.

Solution to Problem

The present invention has been made to solve the above-described problems and provides a method for detecting a crystal defect present in a silicon single crystal wafer doped with nitrogen, the silicon single crystal wafer whose initial oxygen concentration is 8 ppma (JEIDA) or lower, the method including the steps of: making a crystal defect of defect size of 25 nm or smaller apparent and detectable by implanting oxygen into the crystal defect by performing heat treatment on the silicon single crystal wafer in an atmosphere of oxygen; and detecting the crystal defect of the silicon single crystal wafer after the heat treatment, wherein a heat treatment temperature in the heat treatment is set such that, when the ratio between the oxygen solid solubility (hereinafter, described simply as the oxygen solid solubility) and the initial oxygen concentration of the silicon single crystal wafer at the time of heat treatment is set at $\alpha$=the oxygen solid solubility/the initial oxygen concentration, $\alpha$ falls within a range from 1 to 3.

As described above, by heat treatment in which a heat treatment temperature is set such that $\alpha$ falls within a range from 1 to 3, it is possible to make apparent most of the crystal defects of a defect size of 25 nm or smaller and detect them. By detecting these crystal defects that were made apparent, the crystal defects whose defect size was 25 nm or smaller can also be detected.

In this case, it is preferable that the heat treatment temperature is set at 900 to 1200° C. and the time during which the heat treatment is performed is set at 10 to 60 minutes.

With such a heat treatment temperature and heat treatment time, it is possible to make apparent a crystal defect of a silicon single crystal wafer more reliably.

Moreover, the present invention is suitable when the doping concentration of nitrogen of the silicon single crystal wafer is set at $1\times10^{13}$ to $1\times10^{15}$ atoms/cm$^3$.

In the silicon single crystal wafer with such a doping concentration of nitrogen, since the size of a crystal defect is particularly small, the method for making a crystal defect apparent and detecting the crystal defect by the present invention is especially effective.

Moreover, the present invention can perform detection of the crystal defect by any one of detection by a particle counter by a light scattering method, detection by a laser microscope of a confocal optical system, and detection by an RIE method.

By the method described above, it is possible to detect a crystal defect that was made apparent by the present invention.

Advantageous Effects of Invention

With a method for detecting a crystal defect according to the present invention, even in a low-oxygen wafer doped with nitrogen, the low-oxygen wafer in which the defect size of a crystal defect is particularly small, it is possible to make a crystal defect of small defect size apparent and detect the crystal defect. By detecting the crystal defect that was made apparent, a defect of a defect size of 25 nm or smaller can also be detected. As a result, it is possible to evaluate more accurately a crystal defect of a low-oxygen wafer doped with nitrogen.

DESCRIPTION OF EMBODIMENTS

Hereinafter, the present invention will be described in detail, but the present invention is not limited to those described below.

First, a mechanism that makes it possible to detect a crystal defect in the present invention will be described.

As mentioned earlier, it has become difficult to detect micro crystal defects such as a BMD, a COP, and a "void" in a silicon single crystal wafer (a low-oxygen wafer) of low oxygen concentration. In particular, in a low-oxygen wafer doped with nitrogen, the defect size is further reduced, which makes it impossible to detect a micro defect such as a "void", in particular, the micro defect smaller than or equal to 25 nm, with the current defect evaluation methods.

As a highly sensitive evaluation method for detecting defects such as micro BMDs and COPs, there are an RIE (Reactive Ion Etching) process by reactive ion etching, a method for inspecting a wafer section by laser scattering (for example, a method using a crystal defect inspection system MO441 manufactured by Raytex Corporation), and the like.

The RIE method has a detection lower limit of about 10 nm and is effective in detecting micro BMDs, but the problem is that a COP with a thin inner-surface oxide film is not detected even when the size of the COP is greater than the detection lower limit.

On the other hand, the laser scattering method for a wafer section cannot obtain information about a wafer surface layer and can be applied only to bulk defect evaluation. Moreover, the problem is that an area to be evaluated is narrow and evaluation of the in-plane distribution of crystal defects cannot be performed.

Thus, in the present invention, first, an inner-surface oxide film is formed in a micro defect by implanting oxygen into a micro crystal defect by performing heat treatment on a silicon single crystal wafer in an atmosphere of oxygen, and the defect size is increased to make the crystal defect apparent. Next, the crystal defect which was made apparent after heat treatment in this manner is detected by a predetermined method.

An absolute requirement for implantation of oxygen in heat treatment for making a crystal defect apparent is that the oxygen solid solubility of a silicon single crystal wafer at a heat treatment temperature is greater than or equal to the initial oxygen concentration of the wafer (the oxygen solid solubility ≥ the initial oxygen concentration). That is, if the solid solubility of oxygen of a wafer is low, it is impossible to implant oxygen into a crystal defect.

As the heat treatment temperature is increased, the oxygen solid solubility of a wafer is increased, which makes it easier to implant oxygen into the wafer.

However, if the heat treatment temperature is too high, even when oxygen is implanted into a wafer, a crystal defect diffuses outward in a temperature rising stage or a crystal defect of small size (when it is much smaller than a critical size) is annihilated, which makes it impossible to perform appropriate evaluation of a crystal defect.

On the other hand, if the heat treatment temperature is too low, the difference between the oxygen solid solubility and the oxygen concentration in a wafer becomes small and it becomes difficult to implant oxygen into a crystal defect, which makes it impossible to make a crystal defect apparent.

As a result, we conceived of the necessity of setting an appropriate heat treatment temperature for the concentration of oxygen in a wafer, that is, setting an appropriate solid solubility of oxygen, and studied the relationship between the oxygen solid solubility/the initial oxygen concentration and the behavior of a crystal defect.

Here, since there are four models: (1) a model that can make a crystal defect apparent, (2) an outward diffusion model, (3) an inward diffusion (defect annihilation) model, and (4) a model that cannot make a crystal defect apparent to a satisfactory extent, these models will be explained with reference to FIGS. 1 to 4.

(1) Model that can Make a Crystal Defect Apparent

Figure 1:
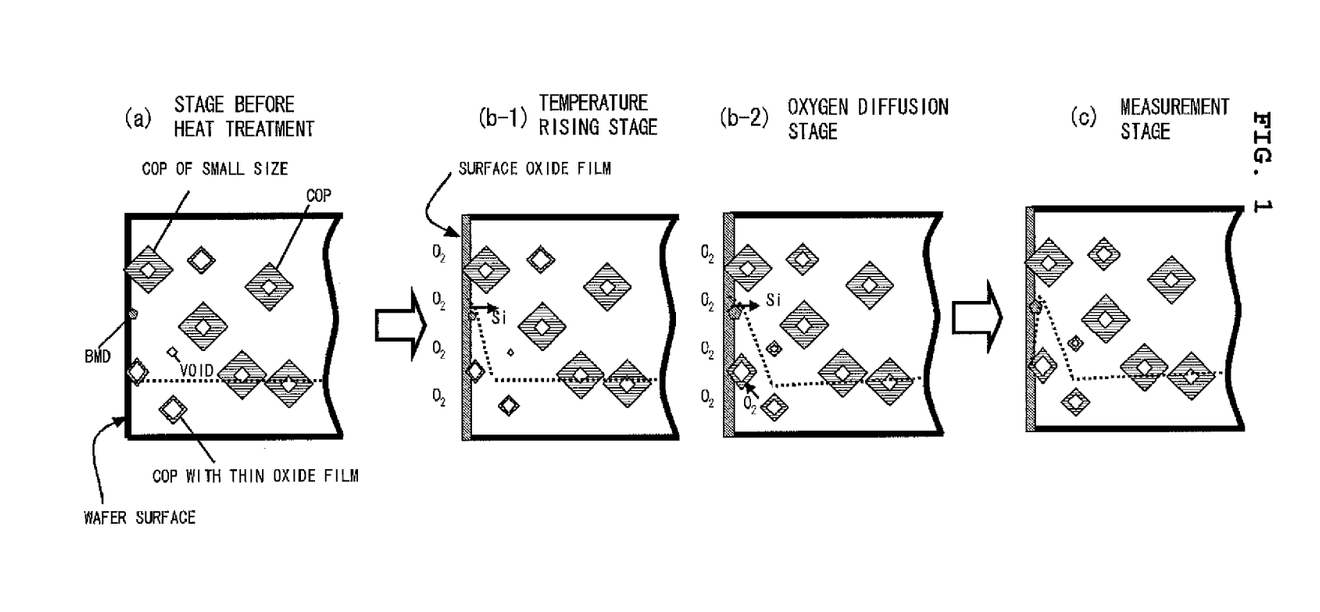
FIG. 1 is a conceptual diagram depicting, as one of models explaining the behavior of a crystal defect by heat treatment, a model that can make a crystal defect apparent by a method of the present invention.

With reference to FIG. 1, a model that can make a crystal defect apparent will be explained. As will be described later, this model holds when 1≤α (=the oxygen solid solubility/the initial oxygen concentration)≤3.

FIG. 1(a) depicts a crystal state of a silicon single crystal wafer in a stage before heat treatment. There are crystal defects such as a COP, a BMD, and a void, and, as the COP, COPs such as a COP of particularly small size and a COP with a thin oxide film are also present.

A change in crystal defects, the change observed when heat treatment is performed on this silicon single crystal wafer (a heat treatment stage), will be explained in a temperature rising stage of FIG. 1(b-1) and in an oxygen diffusion stage of FIG. 1(b-2). In the temperature rising stage, an oxide film is formed on a wafer surface by oxygen in an atmosphere, and interstitial silicon is generated in the wafer. The oxide film of the COP tends to become thinner or the void or the like tends to become smaller as a result of the introduction of interstitial silicon, but they are not annihilated. In a next oxygen diffusion stage, as a result of implantation of oxygen in the atmosphere, the inner-surface oxide film of the COP gets thicker, the size of the BMD is increased, and an oxide film is formed on the inner surface of the void. As a result, each crystal defect is made apparent.

As described above, the heat treatment in an atmosphere of oxygen makes the crystal defects apparent, which makes it possible to detect the crystal defects which were made apparent as depicted in FIG. 1(c).

Incidentally, dotted lines in FIG. 1 indicate a change in oxygen concentration in the drawings, the change obtained by a comparison with a stage before heat treatment. A region in which the crystal defects become apparent is a region in which oxygen was implanted (a region indicating, with dotted lines representing oxygen concentration, that the oxygen concentration became higher than the oxygen concentration before heat treatment).

(2) Outward Diffusion Model

Figure 2:
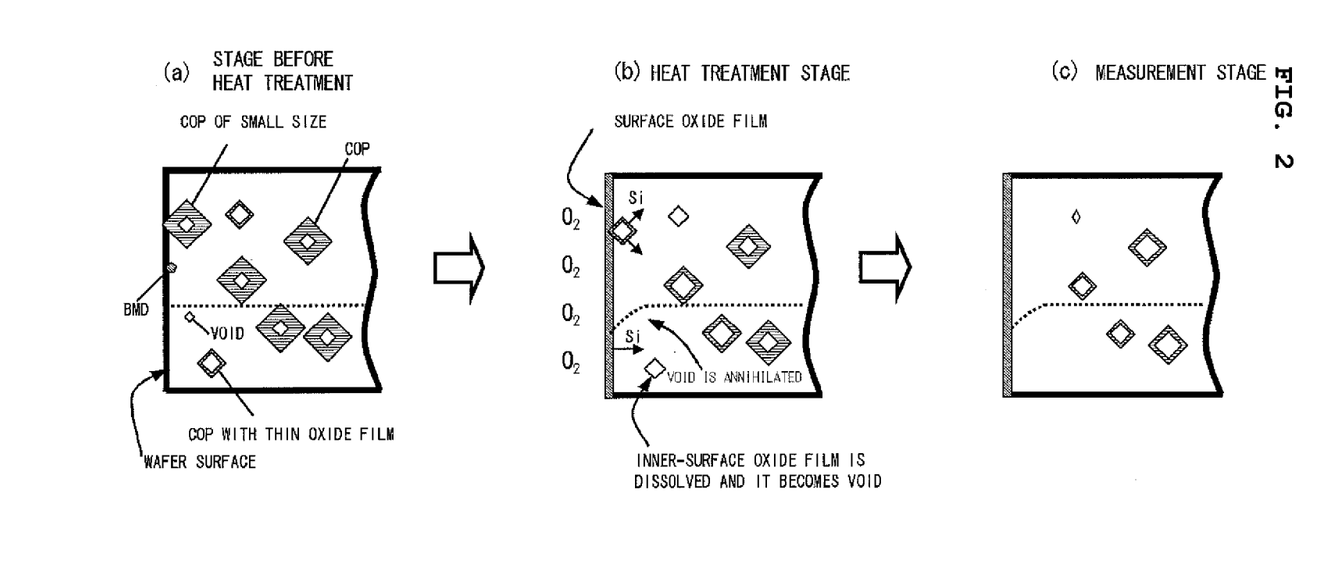
FIG. 2 is a conceptual diagram depicting one of the models explaining the behavior of a crystal defect by heat treatment.

With reference to FIG. 2, a model in which oxygen diffuses outward will be explained. As will be described later, this model holds when the oxygen solid solubility/the initial oxygen concentration=α<1.

As is the case with FIG. 1(a), FIG. 2(a) depicts a crystal state in a stage before heat treatment.

FIG. 2(b) depicts a heat treatment stage. When the oxygen concentration of a silicon single crystal wafer is higher than the oxygen solid solubility of the wafer, an oxide film is formed on the surface, interstitial silicon is generated, and outward diffusion of oxygen present in the wafer surface layer occurs. As a result, the following phenomenon occurs. First, a COP inner-surface oxide film is dissolved by the outward diffusion of oxygen and it becomes a void. Moreover, as a result of implantation of the interstitial silicon, a void is filled in and becomes smaller. Furthermore, a small void is filled in and the crystal defect is annihilated. This changes the defect state and the number of defects in the wafer surface layer part, and therefore it is impossible to perform accurate defect evaluation in this state (refer to FIG. 2(c)).

Incidentally, dotted lines in FIG. 2 indicate a change in oxygen concentration in the drawings, the change obtained by a comparison with the stage before heat treatment. As depicted in the drawings, oxygen in a surface layer portion diffuses outward and is reduced.

(3) Inward Diffusion (Defect Annihilation) Model

Figure 3:
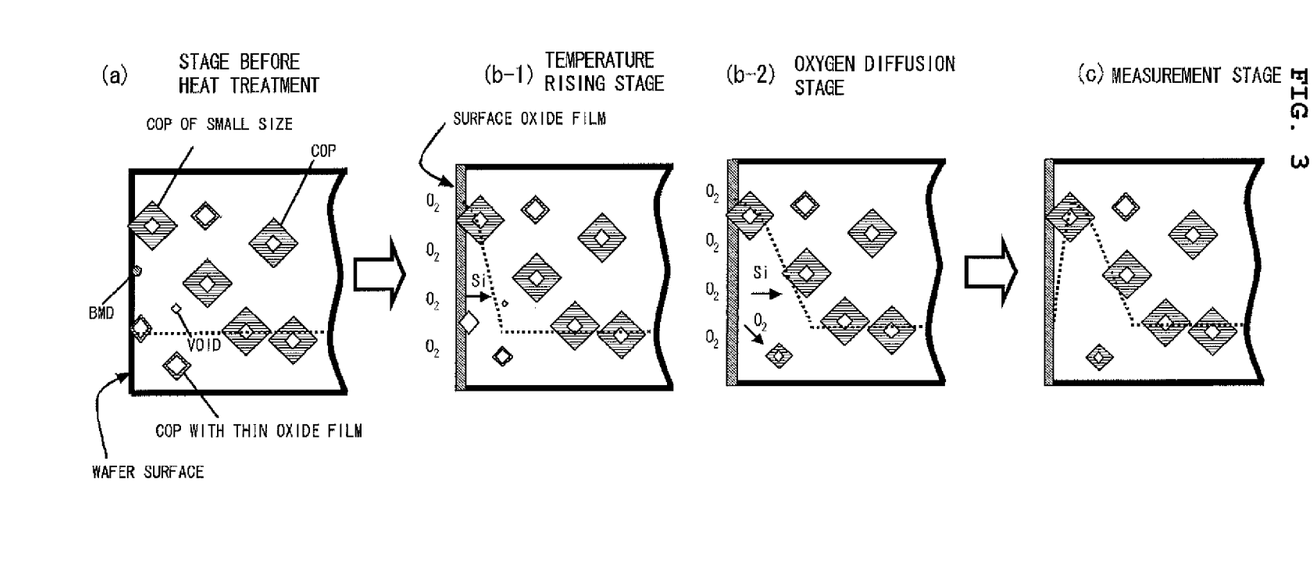
FIG. 3 is a conceptual diagram depicting one of the models explaining the behavior of a crystal defect by heat treatment.

With reference to FIG. 3, a model in which oxygen diffuses inward and a crystal defect is annihilated will be explained. As will be described later, this model holds when the oxygen solid solubility/the initial oxygen concentration=α>3.

As is the case with FIG. 1(a) and FIG. 2(a), FIG. 3(a) depicts a crystal state in a stage before heat treatment.

A change in crystal defects, the change observed when heat treatment is performed on this silicon single crystal wafer (a heat treatment stage), will be explained in a temperature rising stage of FIG. 3(b-1) and in an oxygen diffusion stage of FIG. 3(b-2). When a void of small defect size is present in the wafer, a crystal defect smaller than a critical size is annihilated in the temperature rising stage of (b-1). Moreover, in the oxygen diffusion stage, since the formation of a surface oxide film is promoted and implantation of interstitial silicon becomes predominant, a void is filled in and a void defect is annihilated.

Furthermore, in the wafer surface layer, a crystal defect greater than the critical size is slightly dissolved in the temperature rising stage. However, with the inward diffusion of oxygen, a crystal defect grows (a COP inner-surface oxide film gets thicker, an oxide film is formed on the inner surface of a void, and a BMD also grows).

Dotted lines in FIG. 3 indicate a change in oxygen concentration in the drawings, the change obtained by a comparison with a stage before heat treatment. A region in which the crystal defects become apparent is a region in which oxygen was implanted (a region indicating, with dotted lines representing oxygen concentration, that the oxygen concentration became higher than the oxygen concentration before heat treatment).

In this model, since a surface layer defect is sometimes annihilated as described above, it is impossible to perform accurate evaluation when the surface layer defect is evaluated by using a particle counter by a light scattering method or a laser microscope of a confocal optical system after heat treatment (refer to FIG. 3(c)).

(4) A Model that Cannot Make a Crystal Defect Apparent to a Satisfactory Extent

Figure 4:
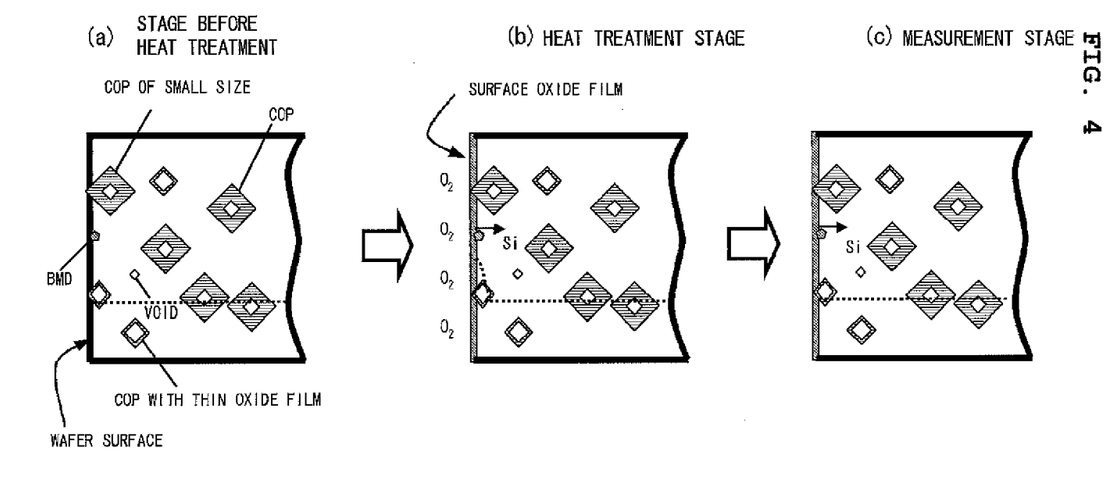
FIG. 4 is a conceptual diagram depicting one of the models explaining the behavior of a crystal defect by heat treatment.

With reference to FIG. 4, a model in which a crystal defect is not made apparent to a satisfactory extent when a heat treatment temperature is too low will be explained. As is the case with FIG. 1(a), FIG. 2(a), and FIG. 3(a), FIG. 4(a) depicts a crystal state in a stage before heat treatment.

FIG. 4(b) depicts a heat treatment stage. When a heat treatment temperature is too low, since a surface oxide film growth rate is slow and the amount of generated interstitial silicon is small, a COP, a BMD, and a void are not annihilated even when they are small in size. Moreover, since an oxygen diffusion coefficient is low, only a tiny amount of oxygen is implanted into the wafer surface layer. As a result, the heat treatment does not affect an original wafer state and is ineffective in making a crystal defect apparent. That is, the wafer in a measurement stage of FIG. 4(c) is hardly changed from the initial wafer of FIG. 4(a).

Dotted lines in FIG. 4 indicate a change in oxygen concentration in the drawings, the change obtained by a comparison with a stage before heat treatment.

(Experiment)

To determine an optimum value of α=the oxygen solid solubility/the initial oxygen concentration for making a crystal defect apparent (a value that is applicable to (1) a model that can make a crystal defect apparent of the above-described models), the following experiment was performed.

By performing evaluations by using a laser microscope (MAGICS manufactured by Lasertec Corporation) of a confocal optical system in a relationship between the heat treatment temperature and the oxygen solid solubility of a wafer doped with nitrogen and various initial oxygen concentrations (1, 3, 5, 8, and 10 ppma (JEIDA)) of a substrate under various heat treatment conditions (temperatures: 900, 1000, 1100, 1200, and 1250° C., time: fixed at 30 minutes, and an atmosphere of oxygen), the presence or absence of the detection of a crystal defect was determined, and the estimation was further done to decide which of the above-described four models each result corresponds to.

By the above-described experiment, the relationship of α=the oxygen solid solubility/the initial oxygen concentration in which a defect can be made apparent was derived. The results are listed in Table 1 below. In Table 1, symbol [○] represents a case in which the crystal defects are increased as compared to the stage before heat treatment, and symbol [x] represents a case in which the crystal defects are reduced or annihilated as compared to the stage before heat treatment. Moreover, a case in which α<1 is estimated to correspond to (2) an outward diffusion model and a case in which α>3 is estimated to corresponds to (3) an inward diffusion (defect annihilation) model. Incidentally, (4) a model that cannot make a crystal defect apparent to a satisfactory extent is estimated to appear at a heat treatment temperature that is much lower than the temperature in this example.

TABLE 1

| Treatment temperature (° C.) | Oxygen solid solubility (ppma) (experimental value) | Substrate oxygen concentration; α = oxygen solid solubility/initial oxygen concentration | | | | |
|---|---|---|---|---|---|---|
| | | 1 ppma | 3 ppma | 5 ppma | 8 ppma | 10 ppma |
| 1250 | 14 | x α: 14 | x α: 4.6 | ○ α: 2.8 | ○ α: 1.75 | ○ α: 1.4 |
| 1200 | 10 | x α: 10 | x α: 3.3 | ○ α: 2.0 | ○ α: 1.25 | ○ α: 1 |
| 1150 | 6.1 | x α: 6.1 | ○ α: 2 | ○ α: 1.2 | x α: 0.76 | x α: 0.61 |
| 1100 | 4.1 | x α: 4.1 | ○ α: 1.3 | x α: 0.82 | x α: 0.51 | x α: 0.41 |
| 900 | 3 | ○ α: 3 | ○ α: 1 | x α: 0.6 | x α: 0.37 | x α: 0.3 |

As a result, it revealed that, when α=the oxygen solid solubility/the initial oxygen concentration, by selecting the heat treatment conditions such that α falls within a range of 1 to 3, appropriate defect evaluation can be performed even for a silicon single crystal wafer doped with nitrogen, the silicon single crystal wafer of low oxygen concentration.

From the above perspective, in the present invention, to make apparent a crystal defect present in a silicon single crystal wafer doped with nitrogen, the silicon single crystal wafer whose initial oxygen concentration is 8 ppma (JEIDA) or lower, heat treatment is performed in an atmosphere of oxygen in the following manner. When the ratio between the oxygen solid solubility and the initial oxygen concentration of a silicon single crystal wafer at the time of heat treatment is set at α=the oxygen solid solubility/the initial oxygen concentration, by performing heat treatment on a silicon single crystal wafer in an atmosphere of oxygen by setting a heat treatment temperature in the heat treatment such that α falls within a range from 1 to 3, oxygen is implanted into a crystal defect and a crystal defect of a defect size of 25 nm or smaller is made apparent to make it possible to detect the crystal defect. By so doing, it is possible to make apparent most of the crystal defects of a defect size of 25 nm or smaller and detect them. By detecting these crystal defects that were made apparent, the crystal defects whose defect size was 25 nm or smaller can also be detected.

By setting the heat treatment conditions for making a crystal defect apparent in such a way that the temperature is set at 900 to 1200° C. and the time is set at 10 to 60 minutes, appropriate oxygen solid solubility is obtained and oxygen can be implanted into a crystal defect, whereby it is possible to make a crystal defect of a silicon single crystal wafer apparent more reliably.

The present invention can be applied to any low-oxygen wafers doped with nitrogen and is particularly suitable for a case in which the doping concentration of nitrogen is $1\times10^{13}$ to $1\times10^{15}$ atoms/cm$^3$. In a silicon single crystal wafer containing such a doping concentration of nitrogen, the size of a crystal defect is particularly small, and therefore a method for making a crystal defect apparent and detecting the crystal defect by the present invention is especially effective.

As a method for detecting a crystal defect that was made apparent in this manner, a publicly known method can be appropriately adopted. In particular, detection can be performed by detection by a particle counter by a light scattering method, detection by a laser microscope of a confocal optical system, detection by the RIE method, and the like. For example, as the particle counter by a light scattering method, SP-1 manufactured by KLA-Tencor Corporation can be used, and, as the laser microscope of the confocal optical system, apparatuses such as MAGICS manufactured by Lasertec Corporation can be used.

Moreover, to detect a crystal defect that was made apparent by the present invention, an oxide contained in the crystal defect that was made apparent may be removed by HF etching. The oxide contained in the crystal defect that was made apparent is, for example, a thickened oxide film on the inner surface of a COP, a BMD (that is, an oxygen precipitate), an oxide film formed on the inner surface of a void, and the like.

EXAMPLES

Hereinafter, the present invention will be described specifically with examples and comparative examples, but these examples do not limit the present invention.

Examples 1 to 3, Comparative Examples 1 to 3

First, six silicon single crystal wafers, each having a diameter of 200 mm, the silicon single crystal wafers with an oxygen concentration of 4 ppma (JEIDA) and a nitrogen concentration of $3\times10^{13}$ atoms/cm$^3$, the silicon single crystal wafers formed of a V region (which is a region with many vacancies, and a vacancy is a defect of atomic level size, the defect caused by a shortage of silicon atoms) were prepared by slicing the same silicon single crystal ingot.

Next, heat treatment was performed on five of these wafers after adjusting the heat treatment conditions in such a way that, for the oxygen solid solubility and the initial oxygen concentration, α=the oxygen solid solubility/the initial oxygen concentration became 0.75 (Comparative Example 2), 1 (Example 1), 1.5 (Example 2), 3 (Example 3), and 3.5 (Comparative Example 3). Incidentally, for comparison, heat treatment to make a crystal defect apparent was not performed on one of the prepared six wafers (Comparative Example 1). A specific heat treatment condition was an atmosphere of oxygen and it was performed with the temperature and the time set at conditions listed in Table 2 below.

Crystal defects of the wafers of the examples and the comparative examples after heat treatment (however, heat treatment was not performed in Comparative Example 1) were evaluated by using a laser microscope (MAGICS manufactured by Lasertec Corporation) of a confocal optical system.

Figure 5:
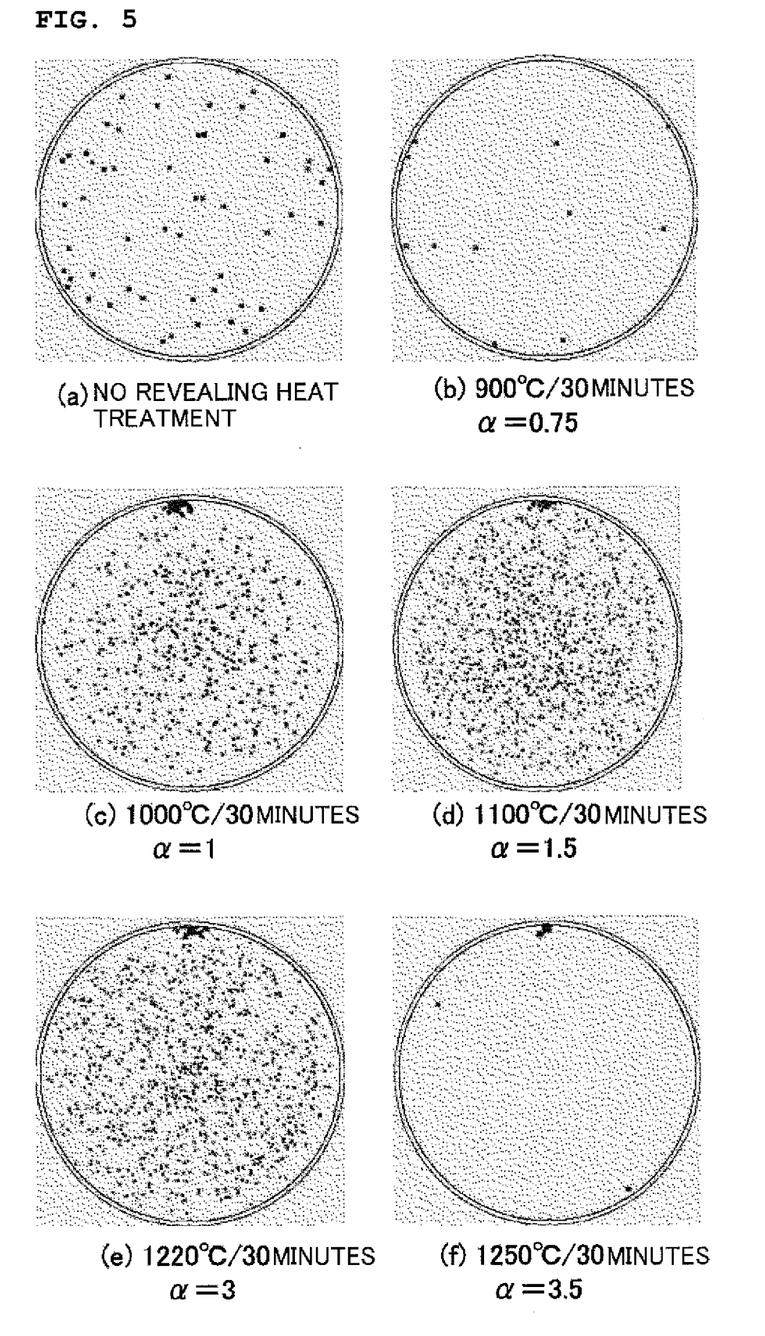
FIG. 5 depicts images obtained when a surface defect is detected by using MAGICS manufactured by Lasertec Corporation in examples and comparative examples.

In FIG. 5, images of the surface defect detection results are depicted. It was revealed that, in Examples 1 to 3, that is, when α was 1, 1.5, and 3, more crystal defects were detected as compared to the wafer (Comparative Example 1) on which heat treatment was not performed and crystal defects of micro size were made apparent. On the other hand, in Comparative Examples 2 and 3, that is, when α was 0.75 and 3.5, crystal defects were reduced as compared to the wafer (Comparative Example 1) on which heat treatment was not performed and the objective of making a crystal defect apparent was not accomplished.

The above results are listed in Table 2 below.

TABLE 2

| | Heat treatment temperature (° C.) | Heat treatment time (minutes) | α | Defect detection image | Evaluation of crystal defect of micro size is possible or impossible? |
|---|---|---|---|---|---|
| Comparative Example 1 | — | — | — | FIG. 5(a) | Accurate evaluation is impossible |
| Comparative Example 2 | 900 | 30 | 0.75 | FIG. 5(b) | Accurate evaluation is impossible |
| Example 1 | 1000 | 30 | 1 | FIG. 5(c) | Evaluation is possible |
| Example 2 | 1100 | 30 | 1.5 | FIG. 5(d) | Evaluation is possible |
| Example 3 | 1220 | 30 | 3 | FIG. 5(e) | Evaluation is impossible |
| Comparative Example 3 | 1250 | 30 | 3.5 | FIG. 5(f) | Accurate evaluation is impossible |

It is to be understood that the present invention is not limited in any way by the embodiment thereof described above. The above embodiment is merely an example, and anything that has substantially the same structure as the technical idea recited in the claims of the present invention and that offers similar workings and benefits falls within the technical scope of the present invention.

The invention claimed is:

1. A method for detecting a crystal defect present in a silicon single crystal wafer doped with nitrogen, the silicon single crystal wafer whose initial oxygen concentration is 8 ppma (JEIDA) or lower, the method comprising the steps of:
    making a crystal defect of defect size of 25 nm or smaller apparent and detectable by implanting oxygen into the crystal defect by performing heat treatment on the silicon single crystal wafer in an atmosphere of oxygen; and
    detecting the crystal defect of the silicon single crystal wafer after the heat treatment,
wherein
    a heat treatment temperature in the heat treatment is set such that, when a ratio between an oxygen solid solubility and an initial oxygen concentration of the silicon single crystal wafer at a time of heat treatment is set at α=the oxygen solid solubility/the initial oxygen concentration, α falls within a range from 1 to 3.

2. The method for detecting a crystal defect according to claim 1, wherein
    the heat treatment temperature is set at 900 to 1200° C. and a time during which the heat treatment is performed is set at 10 to 60 minutes.

3. The method for detecting a crystal defect according to claim 2, wherein
    a doping concentration of nitrogen of the silicon single crystal wafer is set at $1 \times 10^{13}$ to $1 \times 10^{15}$ atoms/cm$^3$.

4. The method for detecting a crystal defect according to claim 3, wherein
    detection of the crystal defect is performed by any one of detection by a particle counter by a light scattering method, detection by a laser microscope of a confocal optical system, and detection by an RIE method.

5. The method for detecting a crystal defect according to claim 2, wherein
    detection of the crystal defect is performed by any one of detection by a particle counter by a light scattering method, detection by a laser microscope of a confocal optical system, and detection by an RIE method.

6. The method for detecting a crystal defect according to claim 1, wherein
    a doping concentration of nitrogen of the silicon single crystal wafer is set at $1 \times 10^{13}$ to $1 \times 10^{15}$ atoms/cm$^3$.

7. The method for detecting a crystal defect according to claim 6, wherein
    detection of the crystal defect is performed by any one of detection by a particle counter by a light scattering method, detection by a laser microscope of a confocal optical system, and detection by an RIE method.

8. The method for detecting a crystal defect according to claim 1, wherein
    detection of the crystal defect is performed by any one of detection by a particle counter by a light scattering method, detection by a laser microscope of a confocal optical system, and detection by an RIB method.

* * * * *